US009658162B2

(12) United States Patent
Wickramasinghe (10) Patent No.: US 9,658,162 B2
(45) Date of Patent: May 23, 2017

(54) METHOD AND APPARATUS FOR DIRECT MEASUREMENT OF THE AMPLITUDE AND/OR PHASE OF A MOLECULAR VIBRATION

(71) Applicant: THE REGENTS OF THE UNIVERSITY OF CALIFORNIA, Oakland, CA (US)

(72) Inventor: H. Kumar Wickramasinghe, Irvine, CA (US)

(73) Assignee: The Regents of the University of California, Oakland, CA (US)

(*) Notice: Subject to any disclaimer, the term of this patent is extended or adjusted under 35 U.S.C. 154(b) by 47 days.

(21) Appl. No.: 14/642,655

(22) Filed: Mar. 9, 2015

(65) Prior Publication Data

US 2015/0253248 A1 Sep. 10, 2015

Related U.S. Application Data

(60) Provisional application No. 61/949,973, filed on Mar. 7, 2014.

(51) Int. Cl.
*G01N 21/65* (2006.01)
*G01J 3/44* (2006.01)
*G01J 3/45* (2006.01)
*G01Q 30/02* (2010.01)

(52) U.S. Cl.
CPC ............ *G01N 21/65* (2013.01); *G01J 3/44* (2013.01); *G01J 3/45* (2013.01); *G01Q 30/02* (2013.01); *G01N 2021/655* (2013.01)

(58) Field of Classification Search
CPC .............................. G01N 21/65; G01Q 30/02
See application file for complete search history.

(56) References Cited

U.S. PATENT DOCUMENTS

| | | | |
|---|---|---|---|
| 9,046,492 B1* | 6/2015 | Prater | G01N 21/658 |
| 2006/0066848 A1* | 3/2006 | Frankel | G01J 3/44 356/301 |
| 2014/0253919 A1* | 9/2014 | Yui | G01J 3/44 356/301 |
| 2014/0268131 A1* | 9/2014 | Tamada | G01N 21/65 356/301 |
| 2014/0310839 A1* | 10/2014 | Wickramasinghe | G01Q 30/02 850/40 |

OTHER PUBLICATIONS

Wickramasinghe, H. Kumar, et al. "Billion-fold increase in tip-enhanced Raman signal." ACS nano 8.4 (2014): 3421-3426.*
Ichimura, Taro, et al. "Tip-enhanced coherent anti-Stokes Raman scattering for vibrational nanoimaging." Physical review letters 92.22 (2004): 220801.*

(Continued)

*Primary Examiner* — Kara E Geisel
*Assistant Examiner* — Shawn Decenzo (57) ABSTRACT

An apparatus and method for measuring amplitude and/or phase of a molecular vibration uses a polarization modulated pump beam and a stimulating Stokes beam on a probe of a scanning probe microscope to detect a Raman scattered Stokes beam from the sample. The detected Raman scattered Stokes beam is used to derive at least one of the amplitude and the phase of the molecular vibration.

22 Claims, 11 Drawing Sheets

(56) References Cited

OTHER PUBLICATIONS

Hayazawa, Norihiko, et al. "Metallized tip amplification of near-field Raman scattering." Optics Communications 183.1 (2000): 333-336.*

Freudiger, Christian W., et al. "Highly specific label-free molecular imaging with spectrally tailored excitation-stimulated Raman scattering (STE-SRS) microscopy." Nature photonics 5.2 (2011): 103-109.*

* cited by examiner

METHOD AND APPARATUS FOR DIRECT MEASUREMENT OF THE AMPLITUDE AND/OR PHASE OF A MOLECULAR VIBRATION

CROSS REFERENCE TO RELATED APPLICATION

This application is entitled to the benefit of U.S. Provisional Patent Application Ser. No. 61/949,973, filed on Mar. 7, 2014, which is incorporated herein by reference.

GOVERNMENT SUPPORT

This invention was made with Government support under Grant No. CHE0802913, awarded by the National Science Foundation. The Government has certain rights in this invention.

FIELD OF INVENTION

This invention relates to methods and apparatus for direct measurement of the amplitude and phase of a molecular vibrational resonance in scanning probe microscopy.

BACKGROUND

The past three decades has seen a tremendous increase in activity in the field of scanning probe microscopy (SPM). A sub-field of SPM called near-field scanning optical microscopy (NSOM) or scanning near-field optical microscopy (SNOM) has focused on techniques that surpass the diffraction limit for microscope resolution (~0.5 μm, the wavelength of light) as stipulated by Abbe and Rayleigh; indeed, SNOM having a lateral resolution of 0.01 the wavelength of light has been demonstrated. The approach that has been used to achieve this extraordinary resolution is a technique named scattering scanning near-field optical microscopy—sSNOM or also referred to as apertureless near-field optical microscopy—aNSOM. This technique is essentially based on U.S. Pat. No. 4,947,034 (ref 1). sSNOM working in the infra-red range of the spectrum (5 μm to 20 μm) has demonstrated the ability to measure infra-red absorption spectra of molecules with spatial resolution approaching 10 nm (ref 2). However, molecular resolution cannot currently be achieved due to poor signal to noise ratio—which gets worse as the wavelength of the probing radiation is increased. Furthermore, working in the infra-red is cumbersome requiring expensive tunable lasers and components. An alternative approach to perform molecular spectroscopy is to detect tip enhanced Raman scattering (TERS) (ref 3). In this technique, a laser beam at frequency (op is focused on the gold or silver tip of a scanning probe microscope system (scanning tunneling microscopy (STM) or atomic force microscopy (AFM)). The polarization of the incident laser is arranged such that the electric field oscillation of the incident beam has a component along the axis of the SPM probe tip. The intense field enhancement produced under the tip is scattered by the vibrating molecules (which vibrate at their eigen frequencies $\omega_{m1}$, $\omega_{m2}$, $\omega_{m3}$ etc). A small fraction ($10^{-7}$) of the incident power at $\omega_P$ is converted into frequencies that are both up shifted ($\omega_P+\omega_{m1}$, $\omega_P+\omega_{m2}$, $\omega_P+\omega_{m3}$ etc.) anti-Stokes bands and down shifted ($\omega_P-\omega_{m1}$, $\omega_P-\omega_{m2}$, $\omega_P-\omega_{m3}$ etc) Stokes bands. In TERS microscopy/spectroscopy, the scattered radiation at $\omega_P$ is suppressed using suitable filters while the up shifted or down shifted bands are transmitted and analyzed in a high resolution spectrometer to identify the vibrational modes of the molecule under the tip. TERS has demonstrated the capability to measure the vibrational frequencies of single molecules. However, the detected signals are extremely weak; in the best cases, typically 100 photons/second are detected from a single vibrational resonance and from molecules having very high Raman cross sections. Typically, the molecules have to be driven at or near an electronic resonance to enhance the signal. TERS is unable to measure the phase response of a molecular vibration.

Coherent anti-Stokes Raman and Stokes Raman Scattering techniques have been demonstrated with diffraction limited optics (best resolution is one half the wavelength of light); they have been successfully applied to microscopy and spectroscopy (ref 4). These techniques provide a much improved signal to noise ratio and are capable of measuring Raman spectra without the need for resonant electronic enhancement. Because the techniques rely on third order non-linear processes, they require femtosecond lasers with high peak powers for successful operation. In femtosecond stimulated Raman spectroscopy (FSRS), the entire Raman spectrum can be captured by a single pump-probe pulse pair (ref 5). In FSRS, the Stokes signal is amplified by stimulated emission and because there is a π/2 phase shift of the incoming stimulating beam as it passes through its focus, the Stokes signal constructively interferes with the stimulating beam and appears as a series of peaks on top of the stimulating background. The signal to noise ratio is much enhanced compared with spontaneous Raman detection. In femtosecond pump-probe experiments, phase information about the vibrating molecules can in principle be retrieved by recording the interference signal (as described above) versus frequency and time in conjunction with suitable simulation models. This is however an indirect measure of molecular phase (ref 6).

SUMMARY

An apparatus and method for measuring amplitude and/or phase of a molecular vibration uses a polarization modulated pump beam and a stimulating Stokes beam on a probe of a scanning probe microscope to detect a Raman scattered Stokes beam from the sample. The detected Raman scattered Stokes beam is used to derive at least one of the amplitude and the phase of the molecular vibration.

An apparatus for measuring amplitude and/or phase of a molecular vibration in accordance with an embodiment of the invention comprises a mechanism configured to displace a probe of a scanning probe microscope to approach a sample, a first beam generator configured to generate a polarization modulated pump beam to illuminate the probe, a second beam generator configured to generate a stimulating Stokes beam to introduce a stimulating Stokes beam onto the probe, and an optical detection system configured to detect a Raman scattered Stokes beam from the sample to derive at least one of the amplitude and the phase of the molecular vibration.

A method for measuring amplitude and/or phase of a molecular vibration in accordance with an embodiment of the invention comprises displacing a probe of a scanning probe microscope to approach a sample, illuminating the probe with a polarization modulated pump beam, introducing a stimulating Stokes beam onto the probe, and detecting a Raman scattered Stokes beam from the sample to derive at least one of the amplitude and the phase of the molecular vibration.

Other aspects and advantages of embodiments of the present invention will become apparent from the following detailed description, taken in conjunction with the accompanying drawings, illustrated by way of example of the principles of the invention.

BRIEF DESCRIPTION OF THE DRAWINGS

Throughout the description, similar reference numbers may be used to identify similar elements.

DETAILED DESCRIPTION

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment," "an embodiment," or similar language means that a particular feature, structure, or characteristic described in connection with the indicated embodiment is included in at least one embodiment of the present invention. Thus, the phrases "in one embodiment," "in an embodiment," and similar language throughout this specification may, but do not necessarily, all refer to the same embodiment.

In this disclosure, different embodiments of a scanning probe microscopy method for the direct measurement of both the amplitude and phase of the vibrational motion of a single molecule (or a group of molecules) are described. These embodiments are based on stimulating the molecular vibrational motion under a metal coated SPM probe tip using continuous wave pump and stimulating lasers that match the desired vibrational resonance. Heterodyne detection can be used with an independent frequency shifted reference optical beam to detect the stimulated Stokes beam from underneath the tip. By using an optically derived electrical reference from the scattered light from the tip end coupled with lock-in detection, both the amplitude and phase of the vibrating molecule under the probe tip can be directly measured immune to microphonics and other thermally induced noise sources.

In a first embodiment (FIG. 1), a pump laser at $f_P$ (25) is directed via optical isolator (24), polarization selector (23), and beam expander (22) toward the long pass dichroic beam splitter (2) which reflects the beam to fill the high numerical aperture (NA) focusing element (1) ((typical NA>0.4). The elements (23), (24), (25) can be viewed as being a pump beam generator. The focusing element focuses the beam at the end of a SPM probe tip (28). The probe tip (28) can be a silicon tip at the end of an AFM cantilever (26) coated with a suitable plasmonic field enhancing film such as gold or silver or it could be a solid gold or silver tip made from electro etched wire or a gold or silver coated wire attached to any of a variety SPM's such as scanning tunneling microscopy (STM), scanning capacitance microscopy (SCM), scanning thermal microscopy (SThM), magnetic force microscopy (MFM) etc. Typical probe tip radius should be at least 20 nm. The tip is made coincident with the focal spot using 3D tip adjust (27). The tip is stabilized over a sample using a standard SPM controller-computer feedback loop (19) coupled with a piezo XYZ scan stage (29). The elements (27) and (29) can be viewed as being a mechanism that can displace the probe about a sample in any desired direction.

Figure 1:
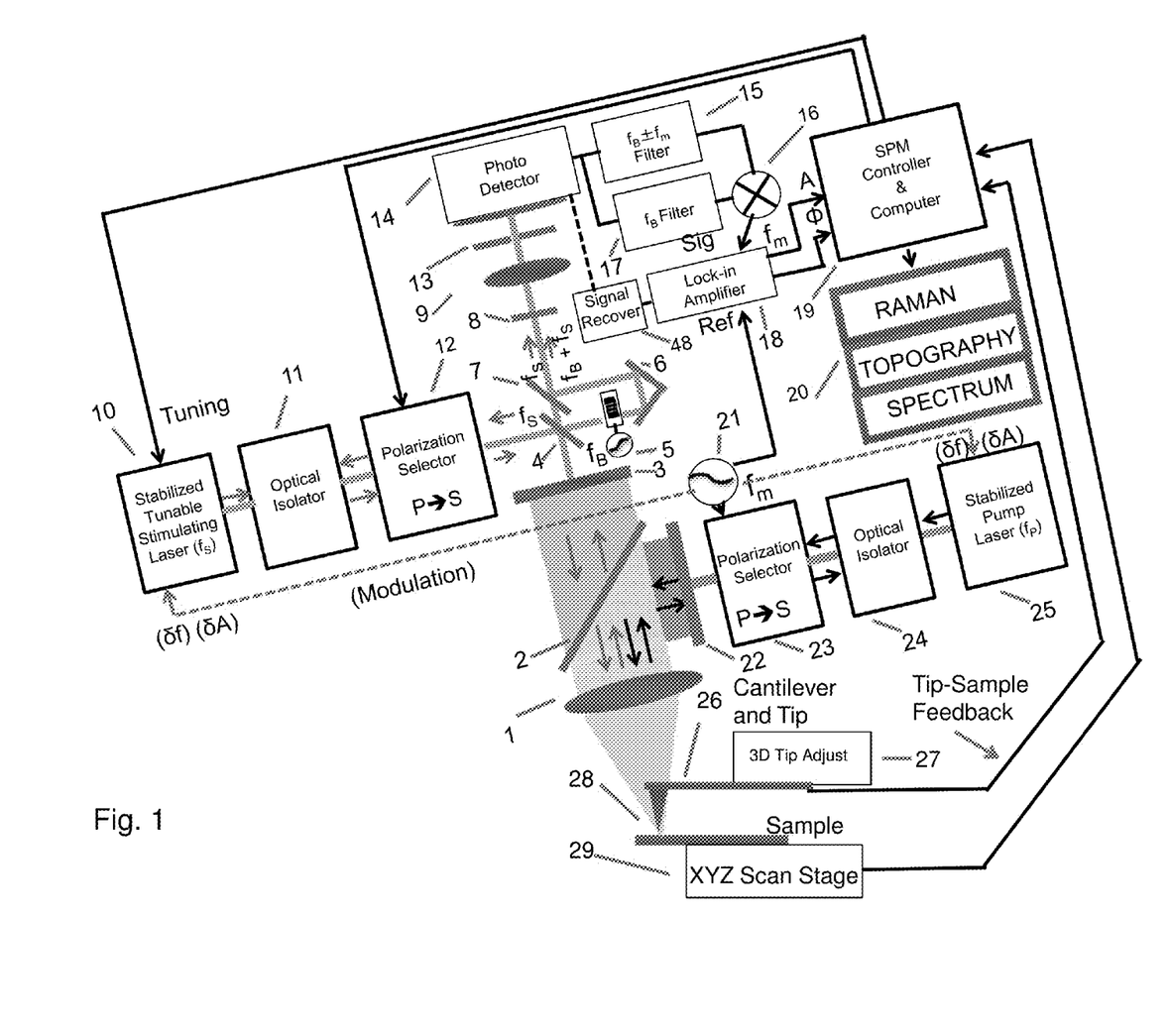
FIG. 1 is a diagram of an apparatus for measuring the amplitude and phase of a molecular vibration in accordance with an embodiment of the invention.

The stabilized tunable stimulating laser at $f_S$ (10) is directed via optical isolator (11) polarization selector (12), and 50/50 beam splitter (4), reflecting half the beam toward beam expander (3) and dichroic beam splitter (2), which transmits the beam toward focusing element (1) focusing the stimulating beam to the same focal spot as the pump beam.

The elements (10), (11), (12) can be viewed as being a stimulating beam generator. In what follows, it is assumed that the standard relationship $\omega=2\pi f$ for all frequencies f. If the pump beam E field varies as $E_P \cos(\omega_P t+\phi P)$ and the stimulating field varies as $E_S \cos(\omega_S t+\phi_S)$, then the driving force for the molecular nuclear oscillations Q will be proportional to $E_P E_S \cos \{\omega_P-\omega_S)t+\phi_P-\phi_S\}$. The time dependence of the driven nuclear vibration Q can be written as $$Q=Q(\Omega)\cos \{\Omega t+\phi_\Omega+(\phi_P-\phi_S)\} \quad (1)$$

where $\phi_\Omega$ is the nuclear oscillation phase with respect to the driving phase $\phi_P-\phi_S$ and $\Omega=(\omega_P-\omega_S)$. $Q(\Omega)$ has an amplitude dependence given by a Lorentzian line shape centered at a specific molecular eigen frequency such as $\omega_{m1}$, $\omega_{m2}$, $\omega_{m3}$ etc. The pump beam $E_P \cos(\omega_P t+\phi_P)$ scatters off the non-linear polarizability generated by this molecular vibration to generate a stimulated Raman beam $E_{STIM}$ given by $$E_{STIM}=AE_P Q(\Omega)\cos(\omega_S t+\phi_S-\phi_\Omega) \quad (2)$$

where A is a constant. It can be seen from equation (2) that the stimulated Stokes beam contains information on both the amplitude $Q(\Omega)$ and phase $\phi_\Omega$ of the molecular oscillation. However, it is noted that the stimulated Stokes beam also contains information about the phase of the stimulating beam $\phi_S$ which will vary with variations in path length of that beam caused by thermal and other noise sources. Thus, an optical reference is needed which varies in phase in exactly the same way as $\phi_S$ in equation (2) in order to recover the vibrational phase $\phi_\Omega$. This is achieved by detecting the Rayleigh scattered stimulating beam from near the end of the probe tip $E_{SCAT}$ given by $$E_{SCAT}=E_{SO} \cos(\omega_S t+\phi_S+\phi_{SCAT}) \quad (3)$$

The phase in equation (3) varies in the same way as the variations in $\phi_S$ in equation (2) aside from a constant phase shift $\phi_{SCAT}$ incurred on scattering from the probe tip. $\phi_{SCAT}=0$ for purely elastic scatterer.

From equations (2) and (3), it can be seen that $E_{STIM}$ varies at the same frequency as $E_{SCAT}$ making it very difficult to separate the information signal $E_{STIM}$ from the optical reference. This separation is achieved by modulating the pump polarization (from P to S) at frequency $f_m$ (typically in the range 10 KHz to 1 MHz) using source (21) which drives polarization selector (23). The polarization selector can be a liquid crystal modulator at the low frequency (10 KHz) range or a pockel cell at the high frequency (1 MHz) range. When the stimulating beam is selected for P polarization using polarization selector (12), and the pump beam polarization oscillates from P to S, a strong stimulated response is observed whenever the pump is at P polarization—due to the enhanced E field from the tip—while negligible stimulated response is observed when the pump is at S polarization—orthogonal to the P polarized stimulating beam. $E_{STIM}$ is then nearly 100% modulated at frequency $f_m$. The resulting beam will have three frequency components $E_{STIM}$, the original stimulated beam at $\omega_S$, $E_{STIU}$, the upper sideband at $(\omega_S+\omega_m)$ and $E_{STIL}$ the lower sideband at $(\omega_S-\omega_m)$.

$$E_{STIM}=AE_P \partial\alpha/\partial q Q(\Omega)\cos(\omega_S t+\phi_S-\phi_\Omega) \quad (2)$$

$$E_{STIU}=0.5AE_P \partial\alpha/\partial q Q(\Omega)\cos \{(\omega_S+\omega_m)t+\phi_S-\phi_\Omega\} \quad (4)$$

$$E_{STIL}=0.5AE_P \partial\alpha/\partial q Q(\Omega)\cos \{(\omega_S-\omega_m)t+\phi_S-\phi_\Omega\} \quad (5)$$

The four optical fields $E_{SCAT}$, $E_{STIM}$, $E_{STIU}$, $E_{STIL}$ return through the focusing element (1), dichroic beam splitter (2), beam expander (3) 50/50 beam splitter (4), 50/50 beam splitter (7), bandpass filter (bandwidth 5 to 10 nm around the stimulating wavelength) (8), focusing element (9) via pinhole (13) to impinge on photo detector (14). The pinhole is chosen so that only the main lobe of the focused spot from lens (9) passes through it.

At the same time, a portion of the stimulating beam from laser (10) that does not get directed toward the focusing element (1) passes through 50/50 beam splitter (4), a frequency shifter (5) (up shifting (or down shifting) the beam by $f_B$), a retro reflecting mirror (6) back to beam splitter (7) where it combines collinearly with the other four beams $E_{STIM}$, $E_{SCAT}$, $E_{STIU}$, $E_{STIL}$. The frequency shifted beam $E_{REF}$ which can be produced by a Bragg cell or a vibrating mirror (as in a serrodyne interferometer or any scheme that produces a phase modulation of the reference arm $E_{REF}$ with respect to the signal arm) constitutes the reference arm of an optical interferometer and has the form $$E_{REF}=E_B \cos \{(\omega_S+\omega_B)t+\phi_B)\} \quad (6)$$

where $\phi_B$ is the phase shift (above $\phi_S$) from the reference path.

At the photo detector (14), which is an optical detector, the frequency shifted reference beam $E_{REF}$ mixes with $E_{STIM}$, $E_{SCAT}$, $E_{STIU}$, $E_{STIL}$ (equations 2, 3, 4, 5) to give photo currents $I_{STIM}$, $I_{SCAT}$, $I_{STIU}$, $I_{STIL}$ at several detectable frequencies given by $$I_{STIM} \propto AE_B E_P \partial\alpha/\partial q Q(\Omega)\cos(\omega_B t+\phi_B-\phi_S+\phi_\Omega) \quad (7)$$

$$I_{STIU} \propto 0.5AE_B E_P \partial\alpha/\partial q Q(\Omega)\cos \{(\omega_B-\omega_m)t+\phi_B-\phi_S+\phi_\Omega\} \quad (8)$$

$$I_{STIL} \propto 0.5AE_B E_P \partial\alpha/\partial q Q(\Omega)\cos \{(\omega_B+\omega_m)t+\phi_B-\phi_S+\phi_\Omega\} \quad (9)$$

$$I_{SCAT} \propto E_B E_{SO} \cos(\omega_B t+\phi_B-\phi_S+\phi_\Omega) \quad (10)$$

There are two components in the detected photo detector current that oscillate at $\omega_B$. $I_{SCAT}$ is typically many orders of magnitude larger than $I_{STIM}$, $I_{STIU}$, $I_{STIL}$. Therefore, $I_{STIM}$ (equation 7) can be safely ignored. $I_{SCAT}$ (equation 10) is used as the reference signal. The photo detector output is filtered to detect either $I_{STIU}$ at $(\omega_B+\omega_m)$ or $I_{STIL}$ at $(\omega_B-\omega_m)$ using filter (15). A separate filter (17) centered at $\omega_B$ detects the $I_{SCAT}$ component from the photo detector. The output of filters (15) and (17) are mixed in a double balanced mixer (16) to recover the molecular vibration signal at $\omega_m$ immune to any phase noise from $\phi_S$. The mixer output yields either $$V_{m-} \propto 0.5AE_{SO} E_B^2 E_P \partial\alpha/\partial q Q(\Omega)\cos \{\omega_m t+(\phi_\Omega+\phi_{SCAT})\} \quad (11)$$

$$V_{m+} \propto 0.5AE_{SO} E_B^2 E_P \partial\alpha/\partial q Q(\Omega)\cos \{\omega_m t-(\phi_\Omega+\phi_{SCAT})\} \quad (12)$$

Once again, it is noted that $\phi_{SCAT}$ is a constant phase shift on scattering of the stimulating beam from the tip end.

Either the signal $V_{m-}$ or $V_{m+}$ can be detected in a lock-in amplifier (18) using a reference at $\omega_m$ from generator (21) to directly yield the amplitude $\partial\alpha/\partial q(\Omega) Q(\Omega)$ and the phase $\phi_\Omega$ of the molecular polarizability at $\Omega$. Since $\partial\alpha/\partial q$ does not vary significantly with $\Omega$, the amplitude or phase of the molecular vibration $Q(\Omega)$ can be recorded using the SPM controller and computer as the sample is raster scanned to record an image and displayed using display (20). Sample topography can be displayed simultaneously using standard SPM software. Furthermore, a stimulated Raman spectrum can be recorded at any point on the sample by locating the probe over that point, tuning the stimulating laser wavelength $f_S$ (10) under SPM computer control, and recording the amplitude of the molecular vibration $Q(\Omega)$ as a function of the stimulating laser wavelength on display (20). The elements for detecting and processing optical signals on the photo detector 14, including the photo detector, can be viewed as being part of an optical detection system. In FIG. 1, these elements include the elements (14)-(20) and (48).

It is noted that instead of filtering the ($\omega_B+\omega_m$) and @B signals from the photo diode and mixing the signals to recover the signal at $\omega_m$, the photodiode output can be passed through suitable signal recovery electronics (48) such as for example a phase or frequency demodulator to recover the signal at $\omega_m$.

The use of modulated P to S polarization on the pump beam provides a major advantage in reducing background noise in the detection system. First, stimulated emission is only present when the pump and stimulating beams have the same polarization; the stimulated response is near zero when the pump polarization is orthogonal to the polarization of the stimulating beam. Second, because from equations (11) and (12) the stimulated signal goes as $E_P^2 E_S$ (since—$Q(\Omega)$ is proportional to $E_P E_S$) and the tip fields can be enhanced by 10-1000 times with respect to the incident fields when they are both P polarized, the stimulated signal can be increased by $10^3$ to $10^9$ times when both pump and probe are P polarized. Therefore, a complete rejection in optical background can be achieved when both the first and second conditions are met simultaneously.

Furthermore, any non-Raman related background can be suppressed during imaging by recording two scans per line—one on top of the other, first with the stimulating beam in P polarization and the second with the stimulating beam in S polarization both selected using polarization selector (12). The difference between the two scans will display the Raman signal free of any background.

Polarization modulation of the pump beam offers another advantage. Since the power flux impinging on the tip/shank is constant during modulation, any thermal instabilities due to transient heating (which would be the case if the pump power was simply intensity modulated) would be minimized; the signal is only present due to the non-linear mixing of the pump and stimulated beam when they interact right at the tip end.

Figure 2:
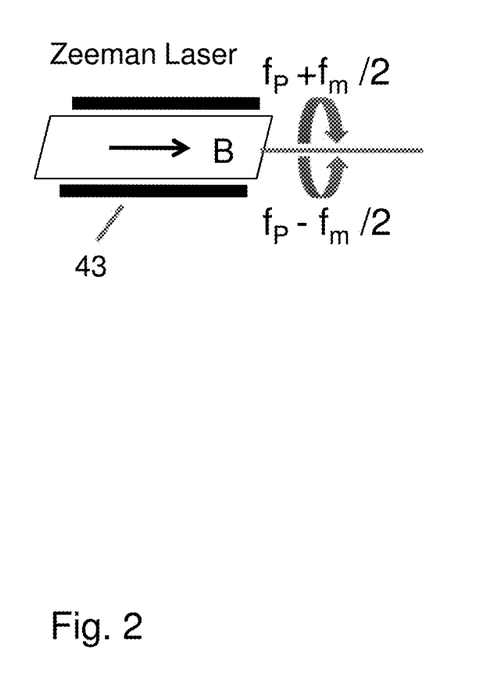
FIG. 2 is a diagram of a Zeeman split laser that can be used in the apparatus shown in FIG. 1 in accordance with an embodiment of the invention.

Different configurations for polarization modulation can be envisaged. In a second embodiment, instead of modulating the pump polarization from P to S at $f_m$ using a polarization modulator, a Zeeman split laser (43) can be used as the pump laser to achieve the same end, as shown in FIG. 2. The Zeeman laser output gives a right circularly polarized beam at $f_P+f_m/2$ and a left circularly polarized beam at $f_P-f_m/2$ that are collinear. When focused on the tip, these two beams together will provide a P polarized modulation at $f_m$.

Figure 3:
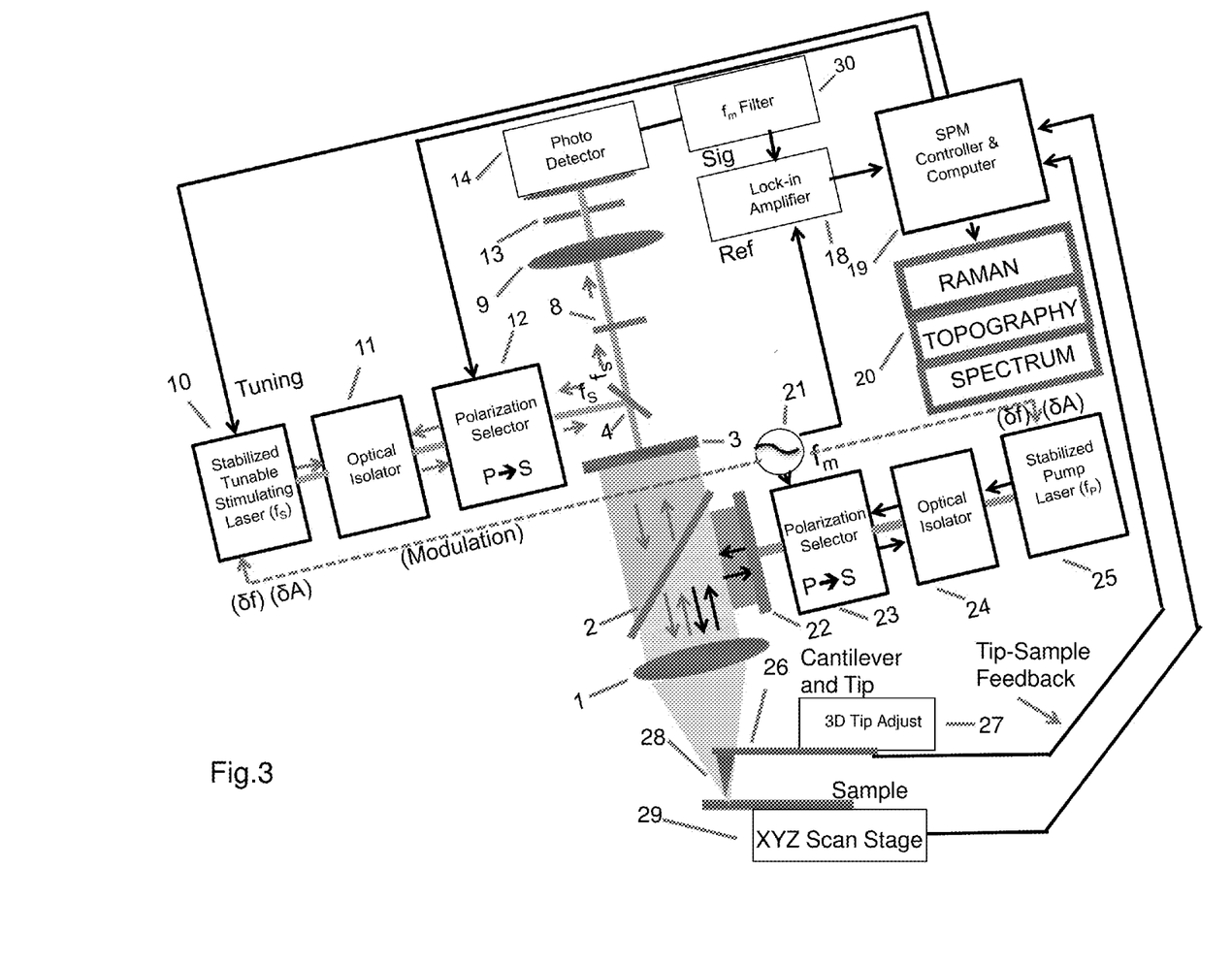
FIG. 3 is a diagram of an apparatus for measuring only the amplitude of a molecular vibration in accordance with an embodiment of the invention.

In a third embodiment, as shown in FIG. 3, the reference arm consisting of elements (4), (5), (6), (7) is removed. The photo detector current then simply measures the intensity modulation at $f_m$. This is followed by filter (30) at $f_m$ and a lock-in amplifier (18). In this embodiment, phase information cannot be measured directly.

Figure 4:
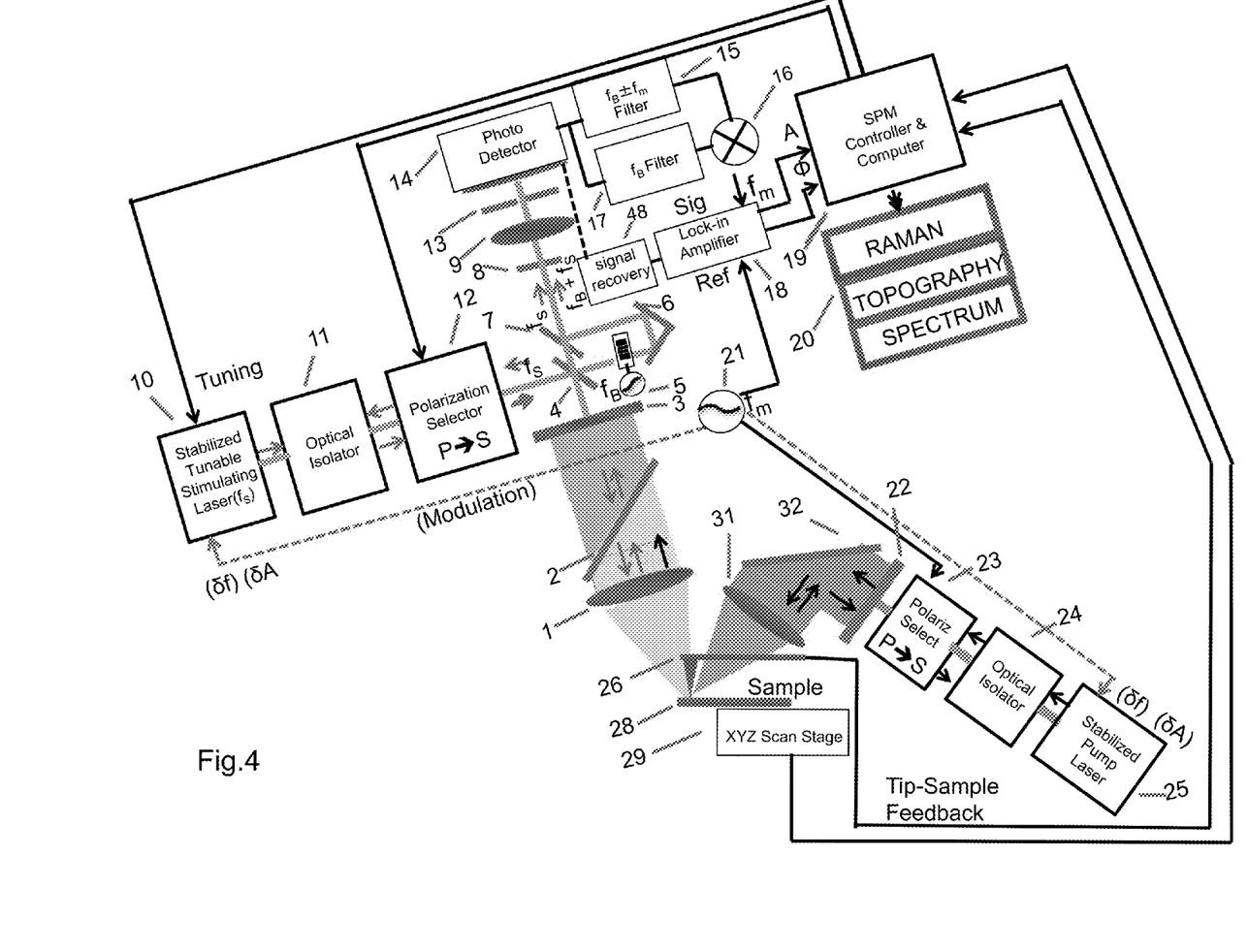
FIG. 4 is a diagram of an apparatus in accordance with another embodiment of the invention.

The fourth embodiment, which is shown in FIG. 4, is similar to the first embodiment except that the pump beam is not collinear with the stimulating beam; it is brought in via mirror (32) and focused onto the tip using focusing element (31). The pump and stimulating beam only interact at the tip end in order to reduce any spurious effects on the Raman signal.

Figure 5:
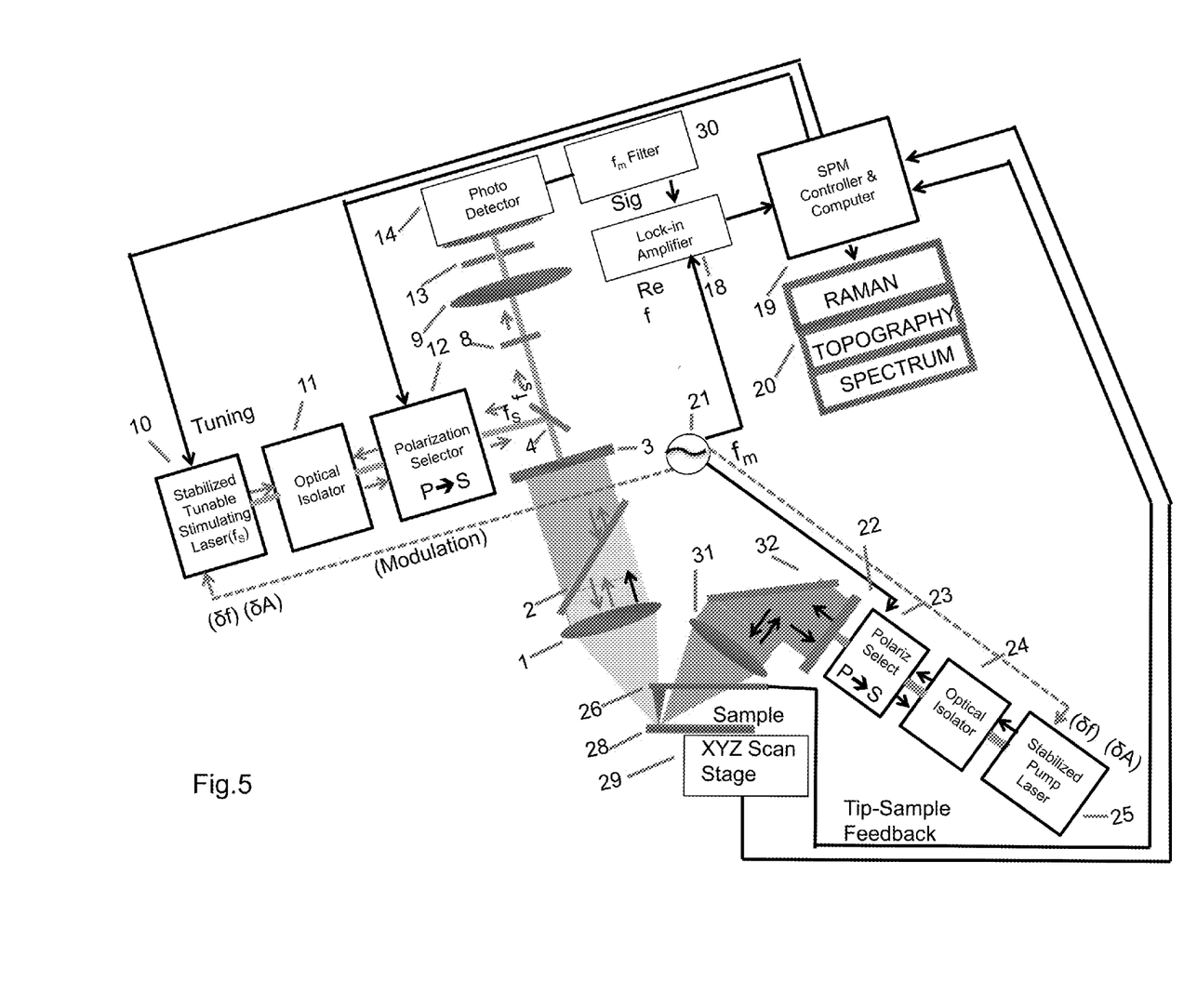
FIG. 5 is a diagram of an apparatus in accordance with still another embodiment of the invention.

The fifth embodiment, which is shown in FIG. 5, is similar to the fourth embodiment except that reference arm (4), (5), (6), (7) is removed. The photo detector current then simply measures the intensity modulation at $f_m$. This is followed by filter (30) at $f_m$ and a lock-in amplifier (18). In this embodiment, phase information cannot be measured directly.

Figure 6:
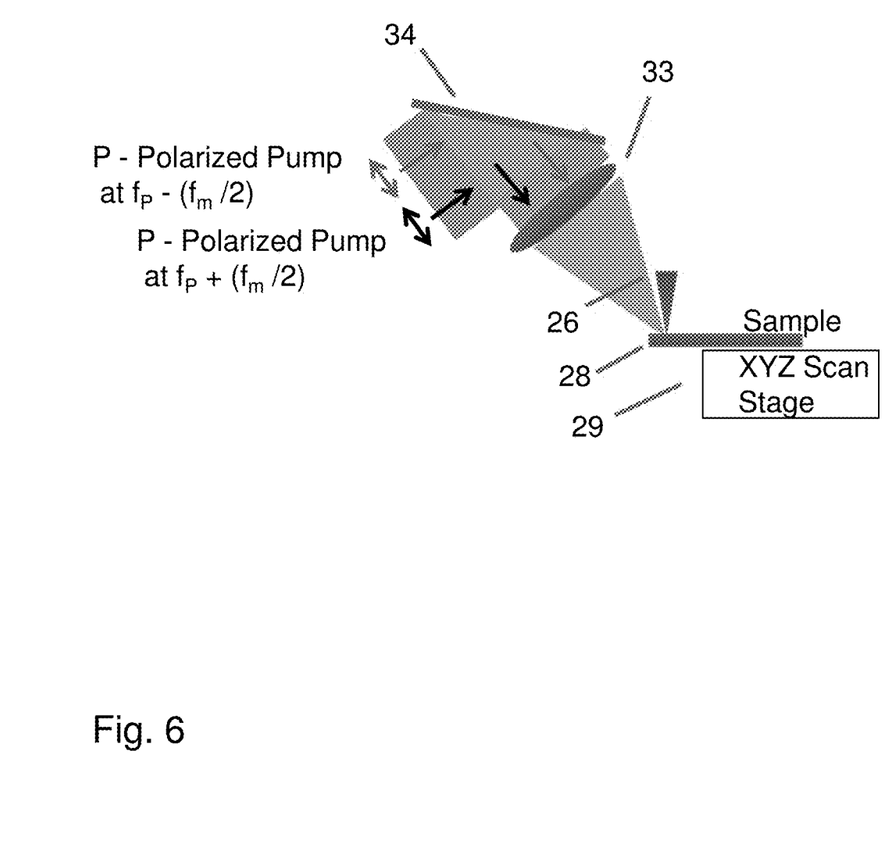
FIG. 6 is a diagram of a pump beam that consists of two collinear P polarized beams in accordance with an embodiment of the invention.

In a sixth embodiment, which is shown in FIG. 6, the pump beam consists of two collinear P polarized beams, one at frequency $f_P+f_m/2$ and the other at $f_P-f_m/2$. The two beams are directed to focusing element (33) and focused onto the tip end (26). The two beams interact at the tip end to produce a P polarization modulation at $f_m$.

Figure 7:
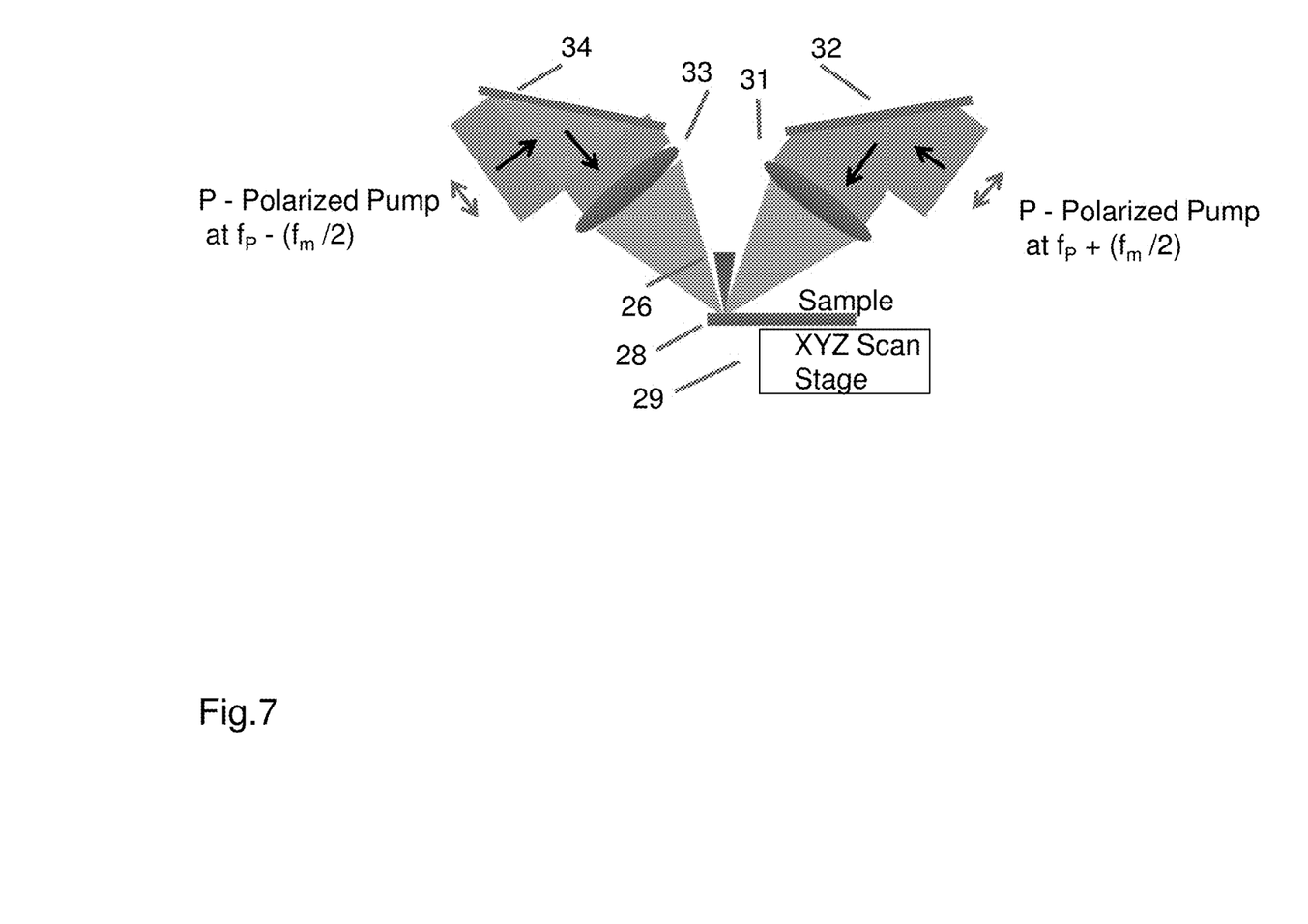
FIG. 7 is a diagram of a pump beam that consists of two non-collinear P polarized beams in accordance with an embodiment of the invention.

The seventh embodiment, which is shown in FIG. 7, is similar to the sixth embodiment except that the pump beam consists of two non-collinear beams; one P polarized beam at $f_P+f_m/2$ directed via mirror (32) and focusing element (31) to a focal spot on the tip end and another P polarized pump beam at $f_P-f_m/2$ directed via mirror (34) and focusing element (33) to the same focal spot on the tip end. The interaction of the two pump beams at the tip end produces a P polarization modulation at $f_m$. The modulation only occurs at the tip end in order to reduce any spurious effects of the Raman signal.

Figure 8:
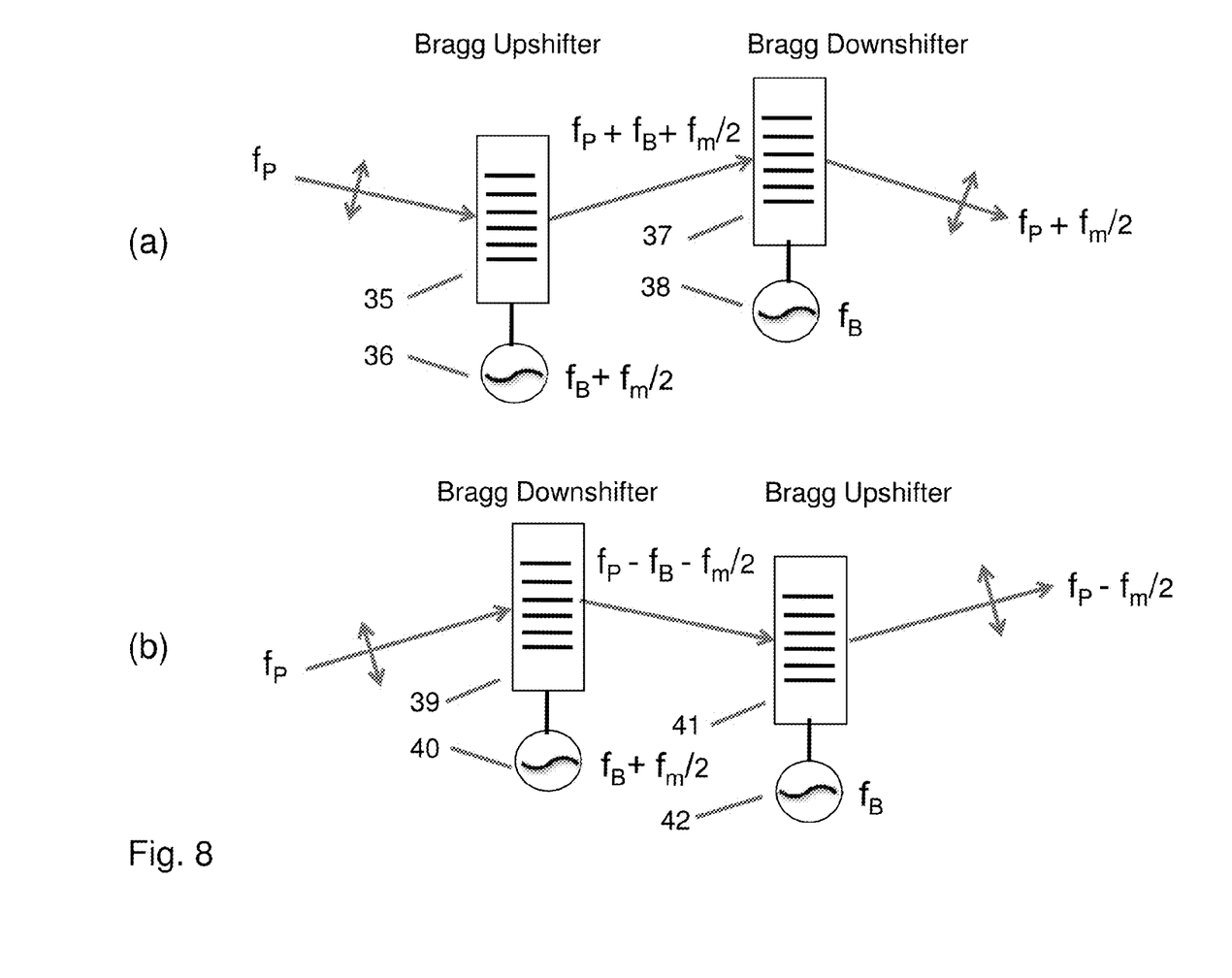
FIG. 8 illustrates a method to produce two P polarized beams in accordance with an embodiment of the invention.

The eighth embodiment, which is shown in FIG. 8, illustrates a method to produce two P polarized beams; one at $f_P+f_m/2$ and the other at $f_P-f_m/2$. In FIG. 8(a), the incident P polarized beam at $f_P$ is incident at the Bragg angle on Bragg cell (35) driven at $f_P+f_m/2$ by signal generator (36). The up-shifted beam $f_P+f_B+f_m/2$ is incident at the Bragg angle on a second Bragg cell (37) driven at $f_B$ by signal generator (36). The down shifted beam is P polarized and has a frequency $f_P+f_m/2$. In FIG. 8(b), the incident P polarized beam at $f_P$ is incident at the Bragg angle on Bragg cell (39) driven at $f_P+f_m/2$ by signal generator (40). The down-shifted beam $f_P-f_B-f_m/2$ is incident at the Bragg angle on a second Bragg cell (41) driven at $f_B$ by signal generator (42). The up-shifted beam is P polarized and has a frequency $f_P-f_m/2$.

Figure 9:
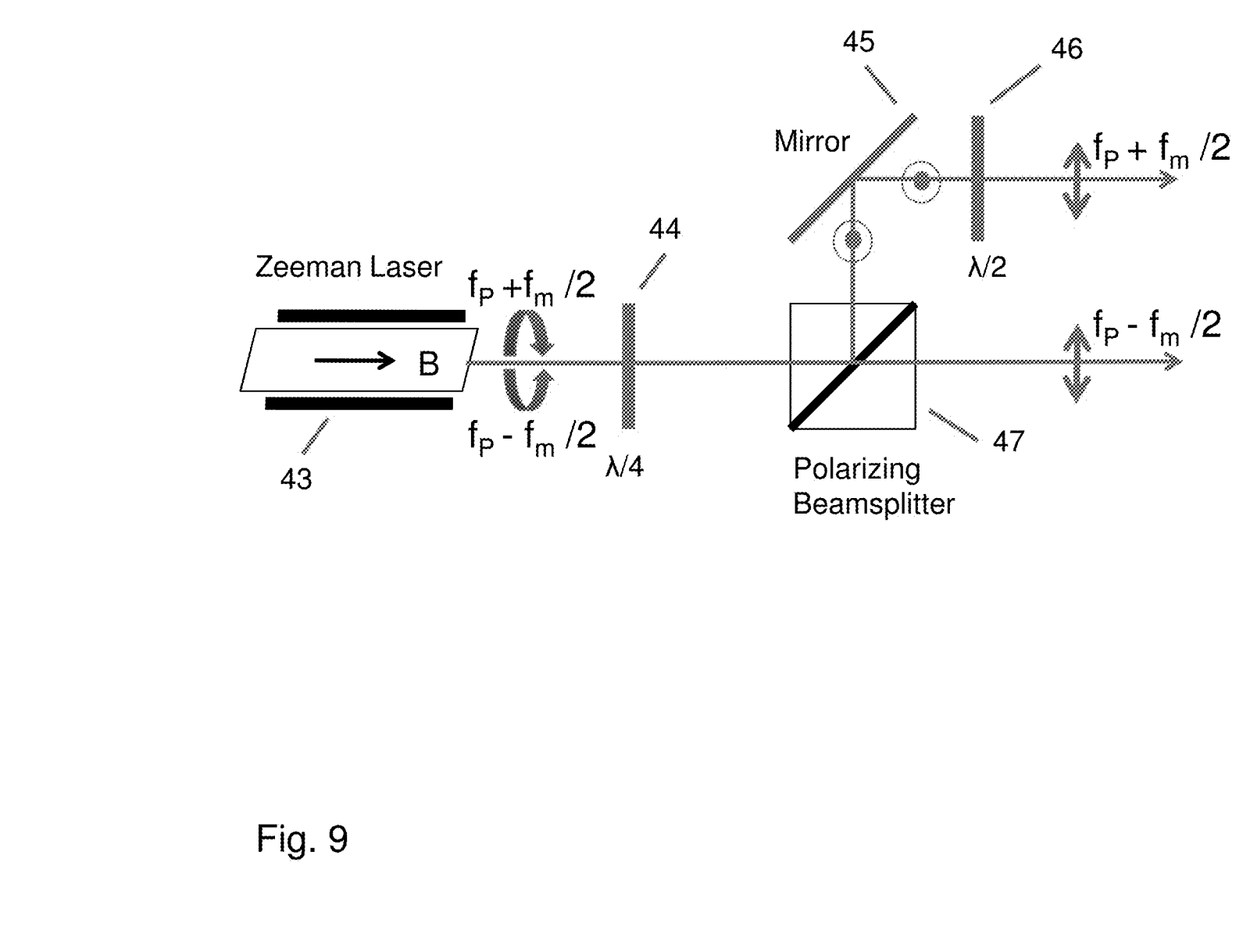
FIG. 9 illustrates a method to produce two P polarized beams in accordance with another embodiment of the invention.

The ninth embodiment, which is shown in FIG. 9, illustrates another method to produce two P polarized beams; one at $f_P+f_m/2$ and the other at $f_P-f_m/2$. A Zeeman split laser (43) is used to produce two circularly polarized beams, one at $f_P+f_m/2$ and one at $f_P-f_m/2$, which are incident on $\lambda/4$ plate (44). The $\lambda/4$ plate converts the two circularly polarized beams into two linear ones—one S polarized and the other P polarized. The two beams are incident on a polarizing beam splitter cube (47) which transmits the P polarized beam at $f_P-f_m/2$ and reflects the S polarized beam at $f_P+f_m/2$. The S polarized beam is reflected off mirror (45) and impinges on $\lambda/2$ plate (46) to covert it to a P polarized beam at $f_P+f_m/2$.

In embodiments illustrated in FIGS. 1, 3, 4 and 5, instead of the P to S polarization modulation of the pump beam, the pump laser can be frequency shifted by $\delta f$ at $f_m$ either by using a diode laser that is current modulated or by modulating the path length within the laser cavity using piezo-electrically driven mirrors. In either case, the peak-peak frequency shift of the pump beam is chosen so that it corresponds to a small frequency modulation $\delta\Omega$ of the Raman drive frequency $\Omega$. $\delta\Omega$ is chosen to be less than half the molecular vibrational linewidth; in wave number space, the Raman linewidths at room temperature are typically 8-10 wave numbers wide. The resulting modulation of the stimulating beam at $f_m$ is detected using the same detection schemes outlined earlier. In the case of frequency modulation however, the displayed spectrum would be the derivative (with respect to wave number) of the normal Raman spectrum.

It should also be noted that, instead of frequency modulation, one could also amplitude modulate the pump laser by δA (25) in embodiments illustrated in FIGS. 1, 3, 4 and 5. This is not the preferred embodiment since optical power modulation focused on the probe tip can cause thermal oscillations and other spurious effects; these effects could be minimized by modulating at high frequencies—above 300 KHz.

It should be noted that the schemes described in embodiments illustrated in FIGS. 1, 3, 4 and 5 would work just as well if we made (10) the pump laser and (25) the stimulating laser. In this case however, we need to make the dichroic mirror (2) a short pass filter transmitting the pump and reflecting the stimulating beam and the bandpass filter (bandwidth 5 to 10 nm) centered around the pump laser frequency rather than the stimulating laser frequency.

Finally, the schemes illustrated in FIGS. 1 and 4 can be adapted to perform pump probe measurements to get dynamic information about molecular vibrations. In the embodiment shown in FIG. 10, both the pump and probe (stimulating) beams are tunable pulses (in the 50 femtosecond to 1 picosecond range). Typically, the pump pulse is chosen to be picosecond in duration while the probe pulse is 50-100 femtoseconds wide. The pump arm is modified as follows. The P polarized pump pulse (25) at $f_P$ is incident via optical isolator (24) onto 50/50 beam splitter (49). Half the beam is transmitted to 50/50 beam splitter (50). The other half which is reflected from beam splitter (49) is reflected off mirror (51), retro reflecting mirror (57), mirror (52), mirror (53), retro reflecting mirror (56), onto Bragg cell (55) where it is frequency shifted by $f_2$. On transmitting through Bragg cell (55), the beam is reflected from mirror (54) onto 50/50 beam splitter (50) where it recombines with the transmitted beam. The stimulating laser (10) is a pulsed laser with pulse duration in the 50-100 femtosecond range. It passes through isolator (11), polarization selector (12) to a 50/50 beam splitter (7) where half the beam is reflected and directed via beam splitter (4), beam expander (3) and dichroic beam splitter (2) to lens (1) where it is focused onto the tip. The transmitted stimulating beam from beam splitter (7) is directed to a retro reflecting delay mirror, followed by a frequency shifter (5) (up shifting (or down shifting) the beam by $f_B$) and then combined with the reflected stimulating pulse from beam splitter (7) where it is also directed to focusing element (1) and focused onto the tip.

Figure 10:
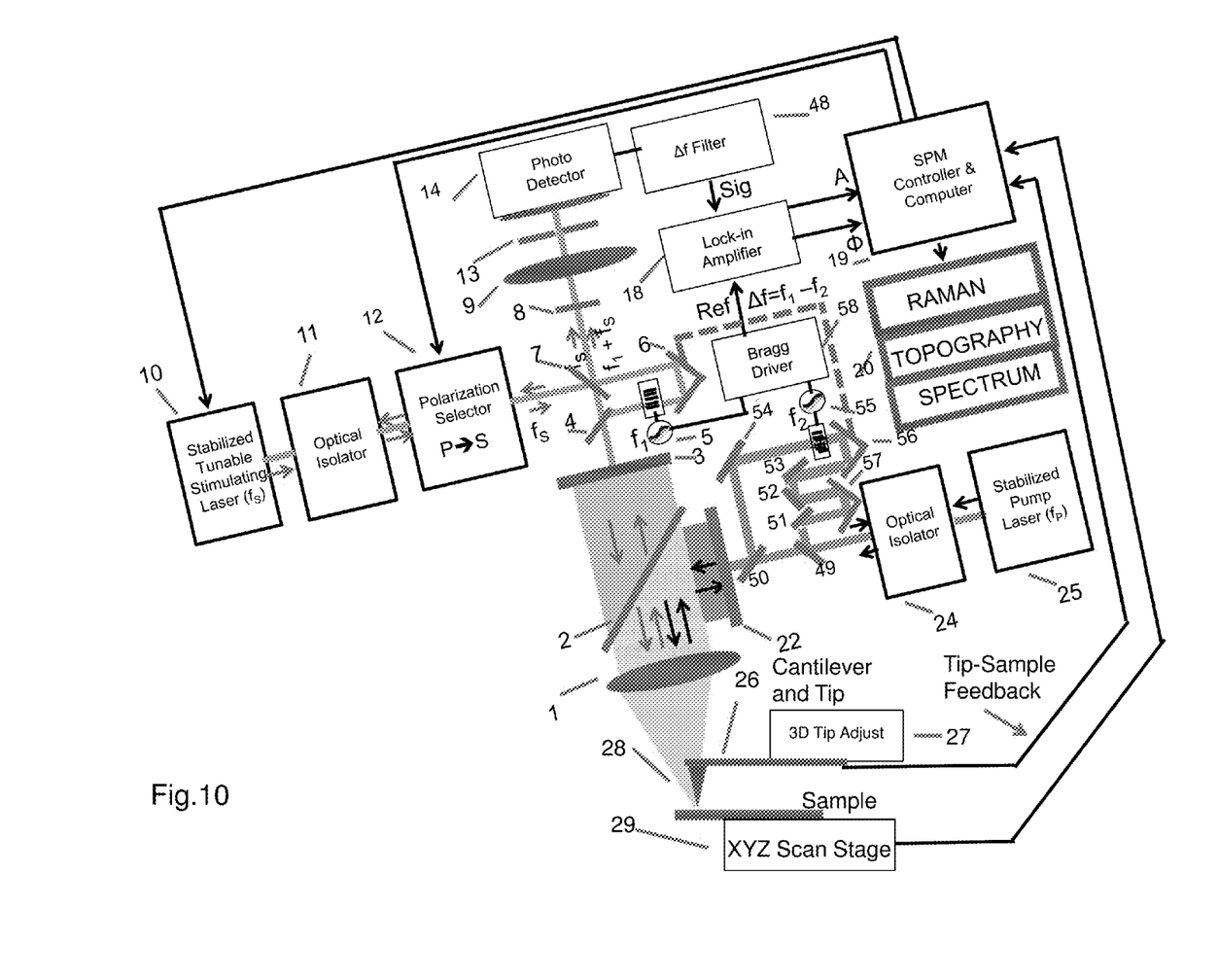
FIG. 10 is a diagram of an apparatus that uses tunable pulses in accordance with an embodiment of the invention.

During operation, the optical path lengths of the pump laser pulse and the stimulating laser pulse are adjusted so that they overlap in time and space at the probe tip using mirror (57). Ganged mirrors (6) and (56) ensure that the frequency shifted pump and the frequency shifted probe pulses overlap as these pulses are delayed with respect to the initial actinic pump/stimulating beam pulse pair. The time dependence of the driven nuclear oscillation Q can be written as $$Q = Q(t)\cos\{\Omega t + \phi_\Omega + (\phi_P - \phi_S)\} \quad (13)$$

where $\phi_\Omega$ is the nuclear oscillation phase at time t with respect to the constant driving phase $(\phi_P - \phi_S)$ and $\Omega = (\omega_P - \omega_S)$.

In order to monitor the time dependence Q, we scatter the frequency shifted and delayed pump pulse from Bragg cell (55) off the non linear polarizability created by equation (13). If the pump beam varies as $E_P(t-\tau)\cos\{(\omega_P+\omega_1)(t-\tau)+\phi_P\}$, then the scattered beam $E_S$ from the non-linear polarizability $\partial\alpha/\partial q\ Q(t)\cos\{\Omega t + \phi_\Omega + (\phi_P - \phi_S)\}$ varies as $$E_S \propto A\partial\alpha/\partial q Q(t)E_P(t-\tau)\cos\{(\omega_P+\omega_1-\Omega)t+\phi_S-\phi_\Omega-(\omega_P+\omega_1)\tau\}$$

or $$E_S \propto A\partial\alpha/\partial q Q(t)E_P(t-\tau)\cos\{(\omega_1+\omega_S)t+\phi_S-\phi_\Omega-(\omega_P+\omega_1)\tau\} \quad (14)$$

$E_S$ is detected by mixing it with the frequency shifted and delayed stimulating beam from Bragg cell (5) which is focused on the tip and scatters back toward the photo diode and serves as a reference beam $E_{REF}$.

The reflected stimulating reference beam $E_{REF}$ that combines with the delayed Stokes signal from the sample in splitter (7) is given by $$E_{REF} = E_{SR}(t-\tau)\cos\{(\omega_S+\omega_2)(t-\tau)+\phi_S\} \quad (15)$$

where it is assumed that the delayed scattered signal $E_{REF}$ from the tip shank is so close to the tip so that it essentially tracks the phase $\phi_S$ of the original stimulating beam. As used herein, "tip shank" is a shank portion of the probe that is near the very tip of the probe.

The photo detector current from the mixing of $E_{REF}$ (equation 15) with $E_S$ (equation 14) has a component $I_{\Delta\omega}$ at $\Delta\omega = (\omega_1 - \omega_2)$ and is essentially a replica of the molecular vibration amplitude and phase translated to the detectable frequency $(\omega_1 - \omega_2)$.

$$I_{\Delta\omega}(t) \propto E_P(t-\tau)E_{SR}(t-\tau)Q(t)\cos\{(\omega_1-\omega_2)t-\phi_\Omega-\Omega\tau-(\omega_1-\omega_2)\tau\} \quad (16)$$

$I_{\Delta\omega}$ is filtered by filter (48) and detected in a lock-in amplifier using a reference at $(\omega_1 - \omega_2)$ from the Bragg driver (58) to yield the amplitude $Q(t)$ and phase $\phi_\Omega$ of the molecular vibration at a given delay $\tau$.

Alternatively, the in-phase component of the signal $I_{LI}$ from the lock-in amplifier can be detected.

$$I_{LI}(\tau) \propto \int E_P(t-\tau)E_{SR}(t-\tau)Q(t)\cos\{\phi_\Omega+\Omega\tau+(\omega_1-\omega_2)\tau\}dt \quad (17)$$

$I_{LI}(\tau)$ vs the delay $\tau$ are recorded by simultaneously translating the retro reflectors 56 and 6 which are typically attached to the same translation stage.

The Fourier transform of the $I_{LI}(\tau)$ vs $\tau$ interferogram from equation (17) yields the Raman spectrum of the molecule being investigated. The derived Raman spectrum is weighted by the convolution of the Fourier transform of $E_P(t)$ with the Fourier transform of $E_{SR}(t)$.

While the method should work with tapping mode AFM, the preferred SPM modes for this application are shear-force AFM and STM where the tip-sample gap spacing is not changing. Once a tip-sample gap spacing is set, the SPM controller uses the sensor output (tunneling current in the case of STM and frequency shift in the case of shear-force AFM) to maintain a constant gap spacing as the tip is raster scanned relative to the sample surface. The measurement of the amplitude and phase of a molecular vibration is best achieved when the gap spacing can be maintained constant at 1 nm or less as the tip is scanned relative to the sample surface.

While the apparatus described is a scanning one where an array of measurements are acquired to generate an image, it should work equally well for a stationary tip-sample pair.

While the apparatus described involves only one tip, an array of tips can be used to detect the molecular identity of array of molecules. The molecules can be deposited directed onto the end of the tip or deposited onto a substrate and brought close in proximity to the tip array. If the array is periodic, both the pump and stimulating laser beams can be directed to the known locations via telocentric laser scanning system. In addition, the optical detector can be a photodiode array or a CCD array.

While the technique described the detection of stimulated tip-enhanced Raman scattering, which is a third order non-linear process, the similar approach can be used to detect other non-linear optical processes such as sum frequency generation, difference frequency generation, second harmonic generation, third harmonic generation, four-wave mixing, dual-beam two photon absorption, etc. with increased spatial resolution and sensitivity.

Figure 11:
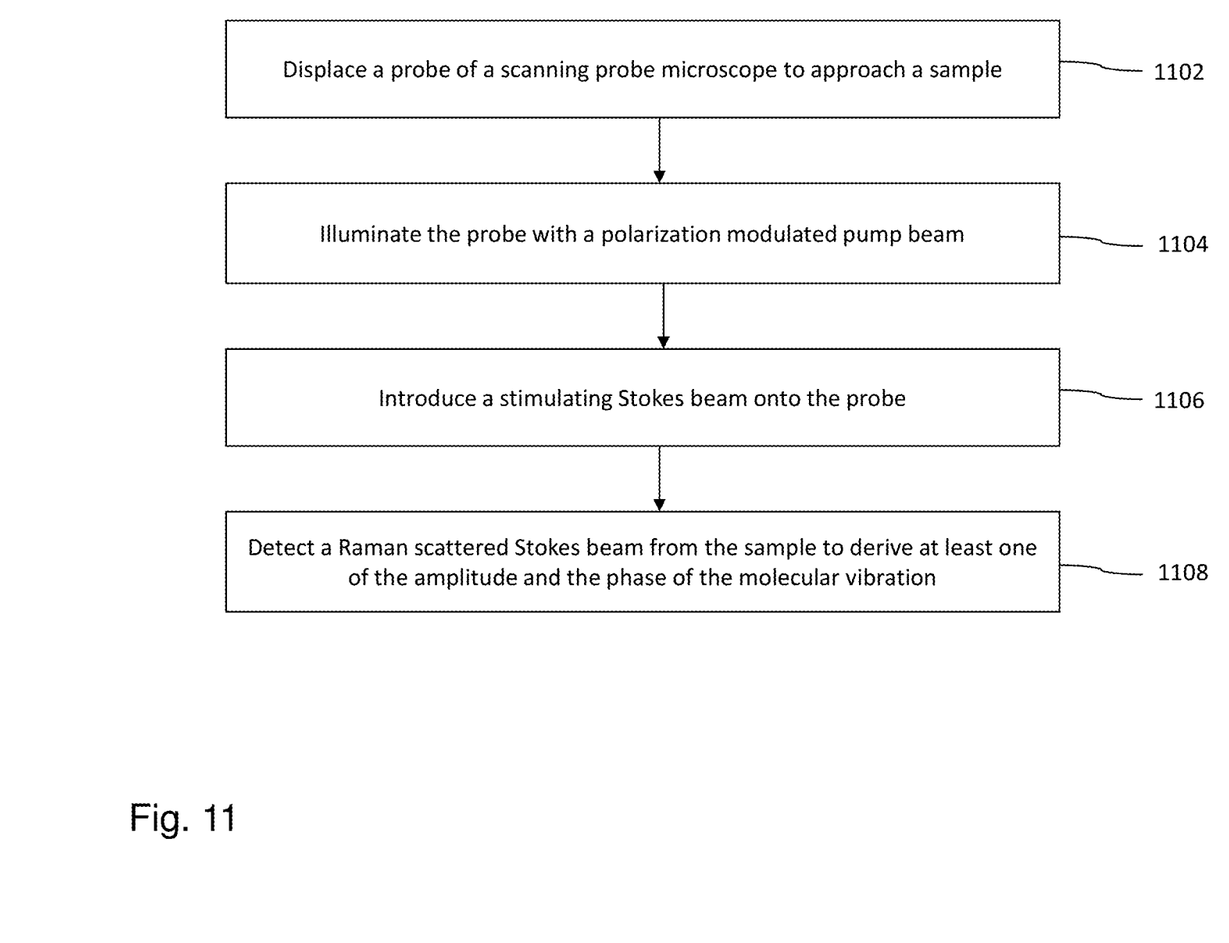
FIG. 11 is a flow diagram of a method for measuring amplitude and/or phase of a molecular vibration in accordance with an embodiment of the invention.

A method for measuring amplitude and/or phase of a molecular vibration in accordance with an embodiment of the invention is described with reference to a flow diagram of FIG. 11. At block (1102), a probe of a scanning probe microscope is displaced to approach a sample. At block (1104), the probe is illuminated with a polarization modulated pump beam. At block (1106), a stimulating Stokes beam is introduced onto the probe. At block (1108), a Raman scattered Stokes beam from the sample is detected to derive at least one of the amplitude and the phase of the molecular vibration.

In the above description, specific details of various embodiments are provided. However, some embodiments may be practiced with less than all of these specific details. In other instances, certain methods, procedures, components, structures, and/or functions are described in no more detail than to enable the various embodiments of the invention, for the sake of brevity and clarity.

Although specific embodiments of the invention have been described and illustrated, the invention is not to be limited to the specific forms or arrangements of parts so described and illustrated. The scope of the invention is to be defined by the claims appended hereto and their equivalents.

REFERENCES

Incorporated Herein by Reference

1) H. K. Wickramasinghe and C. C. Williams, "Apertureless Near Field Optical Microscope", U.S. Pat. No. 4,947,034, issued Aug. 7, 1990.
2) B. Knoll and F. Keilmann, Nature 1999, 399, p. 134
3) B. Pettinger et. al. Annu. Rev. Phys. Chem., 2012, 63, p. 379
4) C. W. Freudiger et. al. Science, 2008, 322, p. 1857
5) D. W. McCamant et. al. Appl. Spectroscopy. 2003, 57(11), p. 1317
6) A. A. Lanin et. al., Scientific Reports, 2013, 3(1842), p. 1

What is claimed is:

1. A method for measuring amplitude and/or phase of a molecular vibration, the method comprising:
displacing a probe of a scanning probe microscope to approach a sample;
illuminating the probe with a polarization modulated pump beam;
introducing a stimulating Stokes beam onto the probe; and
detecting a Raman scattered Stokes beam from the sample to derive at least one of the amplitude and the phase of the molecular vibration.

2. The method according to claim 1, wherein the polarization modulated pump beam is modulated from P polarization to S polarization at frequency fm, which excites one or molecules from ground state to a higher virtual or real state.

3. The method according to claim 1, wherein the stimulating Stokes beam is frequency tuned at frequency fs to amplify a selected Raman mode of the molecules.

4. The method according to claim 1, wherein the Raman scattered Stokes beam is detected using an optical interferometer.

5. The method according to claim 4, wherein the optical interferometer is a heterodyne interferometer or a serrodyne interferometer.

6. The method according to claim 1, wherein a portion of the stimulating Stokes beam is frequency shifted by frequency fB to create a reference arm of a heterodyne interferometer and wherein another portion of the stimulating Stokes beam that is not frequency shifted is focused on the probe.

7. The method according to claim 1, wherein a reference Stokes beam is obtained by back scattered light from the probe.

8. The method according to claim 1, wherein the stimulated Stokes beam from the tip end of the probe and a backscattered Stokes beam from the tip shank of the probe both interfere with a frequency shifted reference beam at frequency fB to create fB+fm and fB−fm sidebands at an optical detector, where fm is the modulation frequency for the polarization modulated pump beam.

9. The method according to claim 8, further comprising filtering and mixing an optically detected signal at the frequency fB and either one of the fB+fm and fB−fm sidebands in a balanced mixer to recover a molecular vibration signal at the frequency fm.

10. The method according to claim 9, wherein the molecular vibration signal at the frequency fm is detected in a lock-in amplifier to recover the amplitude and/or the phase of the molecular vibration.

11. The method according to claim 1, wherein the introducing of the stimulating Stokes beam comprises focusing only a single stimulating Stokes beam on the probe, thereby generating a backscattered Stokes beam from the tip shank of the probe and an amplified Stokes signal from the sample.

12. The method according to claim 1, further comprising detecting optical signal modulation at a polarization modulation frequency fm using an optical detector and displaying the detected optical signal modulation as the amplitude of the molecular vibration.

13. The method according to claim 1, wherein the stimulating Stokes beam has a P polarization or a S polarization.

14. The method according to claim 1, wherein the polarization modulated pump beam is produced by the interference of two frequency shifted P polarized pump beams focused on the tip end of the probe.

15. The method according to claim 1, where the polarization modulated pump beam is a pulse with a width in a picosecond range and the stimulating Stokes beam is in the 50 femtosecond range.

16. The method according to claim 14, wherein the polarization modulated pump beam consists of two pulsed pump beams, where one of the pulsed pump beams is not frequency shifted and the other is frequency shifted by frequency f2 and delayed using a delay path.

17. The method according to claim 15, wherein the stimulating Stokes beam consists of two pulsed beams, wherein one of the two pulsed Stokes beams is frequency shifted by frequency f1 and delayed using a delay path ganged with the same delay path as the delayed pulsed pump beam so that the delayed pulsed Stokes beam overlaps in time and space with the delayed pulsed pump beam.

18. The method of claim 16, further comprising detecting a signal at frequency f1−f2 generated by interference of the two pulsed Stokes beams that are backscattered from the tip end of the probe and the tip shank at an optical detector, the signal at frequency f1−f2 providing the amplitude and phase of the molecular vibration.

19. The method according to claim 17, wherein the amplitude and phase of the signal at frequency f1−f2 is detected using a lock-in amplifier.

20. The method according to claim 18, wherein the output of the lock-in amplifier is recorded as a function of the delay between the delayed pulsed pump beam and the other pulsed pump beam.

21. The method of claim 19, wherein the recorded output of the lock-in amplifier is Fourier transformed to yield the Raman spectrum of the sample beneath the probe.

22. An apparatus for measuring amplitude and/or phase of a molecular vibration, the apparatus comprising:
- a mechanism configured to displace a probe of a scanning probe microscope to approach a sample;
- a first beam generator configured to generate a polarization modulated pump beam to illuminate the probe;
- a second beam generator configured to generate a stimulating Stokes beam to introduce a stimulating Stokes beam onto the probe; and
- an optical detection system configured to detect a Raman scattered Stokes beam from the sample to derive at least one of the amplitude and the phase of the molecular vibration.

\* \* \* \* \*